(12) United States Patent
Abbasi et al.

(10) Patent No.: US 10,743,951 B2
(45) Date of Patent: Aug. 18, 2020

(54) SYSTEMS AND METHODS FOR REPAIRING BONE WITH MULTIPLE TOOLS

(71) Applicant: MAKO Surgical Corporation, Fort Lauderdale, FL (US)

(72) Inventors: Ali Zafar Abbasi, Boca Raton, FL (US); Jonathan Greenwald, Coconut Creek, FL (US); Philip H. Frank, Maplewood, NJ (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 91 days.

(21) Appl. No.: 16/036,669

(22) Filed: Jul. 16, 2018

(65) Prior Publication Data

US 2018/0318022 A1 Nov. 8, 2018

Related U.S. Application Data

(63) Continuation of application No. 14/600,972, filed on Jan. 20, 2015, now Pat. No. 10,045,826.

(51) Int. Cl.
*A61B 34/30* (2016.01)
*A61B 34/37* (2016.01)
*A61B 34/35* (2016.01)
*A61B 34/10* (2016.01)
*A61B 17/16* (2006.01)
*A61B 34/00* (2016.01)
*A61B 34/20* (2016.01)

(52) U.S. Cl.
CPC .............. *A61B 34/30* (2016.02); *A61B 34/10* (2016.02); *A61B 34/35* (2016.02); *A61B 34/37* (2016.02); *A61B 17/16* (2013.01); *A61B 34/25* (2016.02); *A61B 2034/105* (2016.02); *A61B 2034/107* (2016.02); *A61B 2034/2055* (2016.02); *A61B 2034/305* (2016.02)

(58) Field of Classification Search
CPC ....... A61B 17/14; A61B 17/142; A61B 17/15; A61B 17/154; A61B 17/155; A61B 17/157; A61B 17/16; A61B 17/1613; A61B 17/1615; A61B 17/1617; A61B 17/162
USPC .................................................. 606/86 R–89
See application file for complete search history.

(56) References Cited

U.S. PATENT DOCUMENTS

| 5,086,401 A * | 2/1992 | Glassman | B25J 9/1679 700/259 |
| 8,010,180 B2 * | 8/2011 | Quaid | A61B 17/1703 600/424 |
| 8,758,352 B2 * | 6/2014 | Cooper | G16H 40/63 606/87 |

(Continued)

*Primary Examiner* — Eric S Gibson
(74) *Attorney, Agent, or Firm* — Bookoff McAndrews, PLLC

(57) ABSTRACT

A method for repairing a bone of a patient may include superimposing a first virtual boundary on a virtual bone and superimposing a second virtual boundary on the virtual bone. The method may further include robotically modifying the bone of the patient with a planar tool along a first working boundary to create a first surface. The first working boundary may correspond to the first virtual boundary. The method may further include robotically modifying the bone of the patient with a rotary tool along a second working boundary to create a second surface. The second working boundary may correspond to the second virtual boundary.

20 Claims, 7 Drawing Sheets

(56) References Cited

U.S. PATENT DOCUMENTS

| | | | | |
|---|---|---|---|---|
| 8,936,596 B2* | 1/2015 | Mittelstadt | A61B 17/17 | 606/79 |
| 9,002,426 B2* | 4/2015 | Quaid | G06F 19/00 | 600/407 |
| 9,622,823 B2* | 4/2017 | Bozung | A61B 17/3403 | |
| 10,045,826 B2* | 8/2018 | Abbasi | A61B 34/37 | |
| 2008/0147075 A1* | 6/2008 | Bonutti | A61B 17/025 | 606/88 |
| 2009/0012531 A1* | 1/2009 | Quaid | G06F 19/00 | 606/130 |
| 2009/0306676 A1* | 12/2009 | Lang | G06K 9/00 | 606/102 |
| 2010/0217400 A1* | 8/2010 | Nortman | A61F 2/30771 | 623/20.14 |
| 2011/0130761 A1* | 6/2011 | Plaskos | A61B 17/155 | 606/87 |
| 2011/0208256 A1* | 8/2011 | Zuhars | A61F 2/30756 | 606/86 R |
| 2011/0245833 A1* | 10/2011 | Anderson | A61B 17/1626 | 606/80 |
| 2012/0245585 A1* | 9/2012 | Kaiser | A61B 17/1633 | 606/80 |
| 2012/0323244 A1* | 12/2012 | Cheal | A61B 17/155 | 606/87 |
| 2013/0116698 A1* | 5/2013 | Wilkinson | A61B 17/157 | 606/88 |
| 2013/0211531 A1* | 8/2013 | Steines | A61F 2/4684 | 623/20.35 |
| 2014/0012267 A1* | 1/2014 | Sikora | A61F 2/3859 | 606/88 |
| 2014/0180290 A1* | 6/2014 | Otto | A61B 17/15 | 606/80 |
| 2015/0182237 A1* | 7/2015 | Nadzadi | A61B 34/30 | 606/80 |
| 2015/0245878 A1* | 9/2015 | Jaramaz | G16H 20/40 | 606/87 |
| 2015/0245879 A1* | 9/2015 | Nikou | A61B 34/10 | 606/88 |
| 2015/0257768 A1* | 9/2015 | Bonutti | A61B 17/1626 | 606/88 |
| 2015/0342691 A1* | 12/2015 | Otto | A61B 17/1703 | 606/80 |
| 2016/0113720 A1* | 4/2016 | Lavallee | A61B 17/1764 | 606/130 |
| 2016/0135816 A1* | 5/2016 | Lavallee | A61B 17/17 | 606/88 |
| 2016/0206375 A1* | 7/2016 | Abbasi | A61B 34/30 | |
| 2016/0338782 A1* | 11/2016 | Bowling | A61B 34/37 | |
| 2016/0343273 A1* | 11/2016 | Stuart | G09B 23/28 | |
| 2017/0151019 A1* | 6/2017 | Nikou | A61B 17/155 | |
| 2018/0318022 A1* | 11/2018 | Abbasi | A61B 34/30 | |

* cited by examiner

Fig. 9
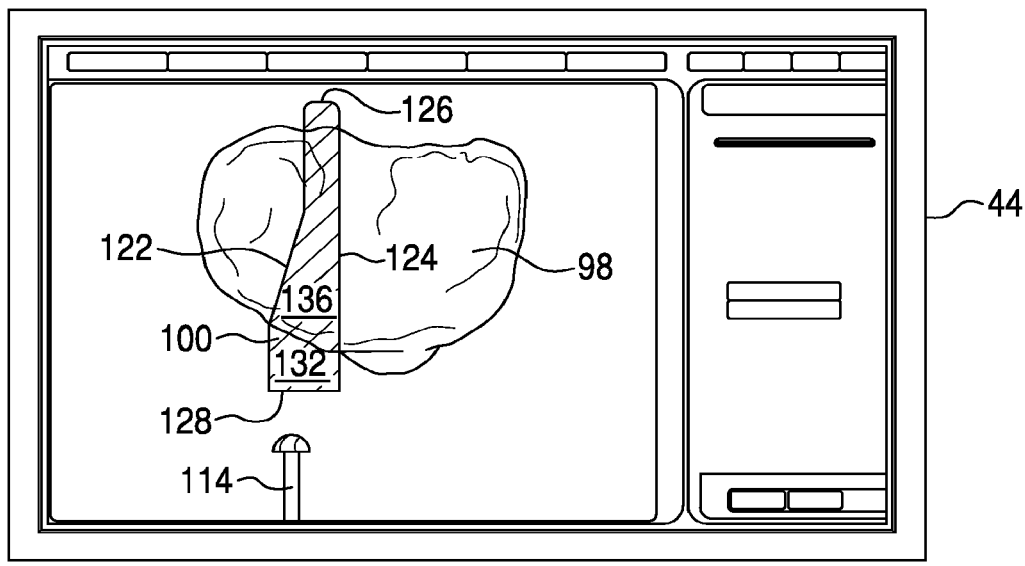
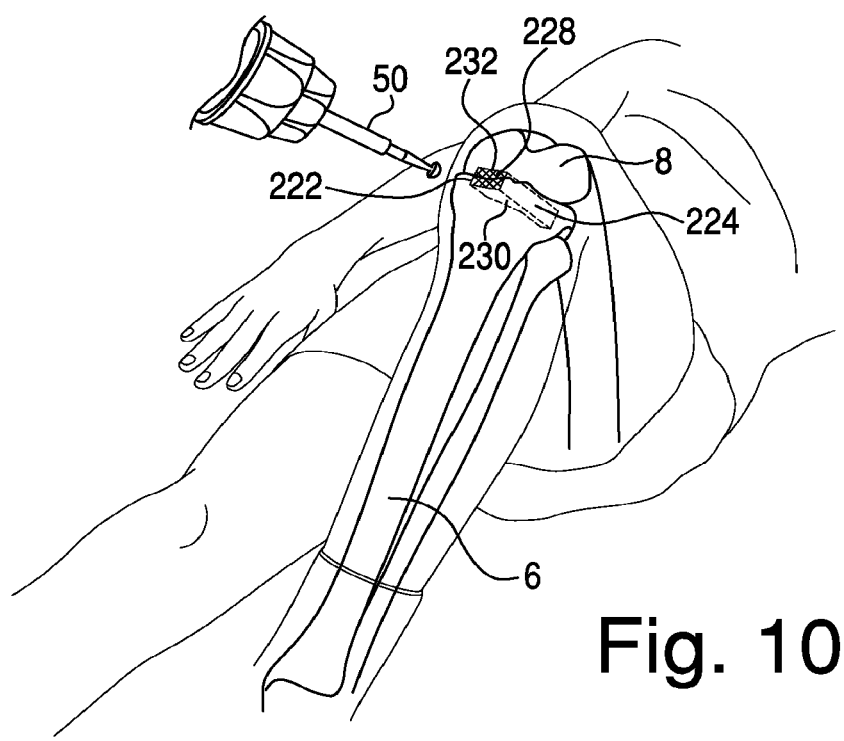
Fig. 10

SYSTEMS AND METHODS FOR REPAIRING BONE WITH MULTIPLE TOOLS

CROSS-REFERENCE TO RELATED APPLICATION(S)

This application is a continuation of pending U.S. application Ser. No. 14/600,972, filed on Jan. 20, 2015, which is incorporated herein by reference in its entirety.

TECHNICAL FIELD

Embodiments of the present disclosure relate generally to medical procedures, and more particularly, to methods and systems for planning and performing bone repair procedures.

BACKGROUND

Robotic surgical systems are currently used to perform bone repair procedures, such as partial knee replacement surgeries. These procedures may be performed using a robotic device having a single tool. After the bone has been prepared, an implant component may be cemented onto the prepared bone. Any deviations between the prepared bone surface and the bone-contacting surface of the implant may be filled with cement. However, to receive a press-fit implant component (e.g., without cement), the bone surfaces must be precisely shaped to receive, and sometimes match, the bone-contacting surfaces of the component. Current methods and tools used to prepare bone may not result in prepared bone surfaces that correspond to the implant surfaces with enough precision to hold a press-fit implant. More precise bone preparation may also improve the fixation of cemented implant components.

SUMMARY

Embodiments of the present disclosure relate to, among other things, methods and systems for planning and performing bone repair procedures. Each of the embodiments disclosed herein may include one or more of the features described in connection with any of the other disclosed embodiments.

A method for repairing a bone of a patient may include superimposing a first virtual boundary on a virtual bone; superimposing a second virtual boundary on the virtual bone; robotically modifying the bone of the patient with a planar tool along a first working boundary to create a first surface, wherein the first working boundary corresponds to the first virtual boundary; and robotically modifying the bone of the patient with a rotary tool along a second working boundary to create a second surface, wherein the second working boundary corresponds to the second virtual boundary.

The method may additionally or alternatively include one or more of the following features or steps: the bone may be a tibia, the first surface may be a tibial floor, and the second surface may be a tibial wall; at least a portion of the tibial wall may be substantially perpendicular to at least a portion of the tibial floor; the first surface may be planar; the planar tool and the rotary tool may be adapted to removably connect to the end of a robotic arm; the method may further include at least one of (a) removing the planar tool from the end of the robotic arm and connecting the rotary tool to the end of the robotic arm, or (b) removing the rotary tool from the end of the robotic arm and connecting the planar tool to the end of the robotic arm; the method may further include securing an implant to the first surface without the use of an adhesive; the implant may be at least partially formed of a porous material; the implant may include a keel; the method may further include, before securing the implant and after creating the first surface, robotically modifying the first surface with a drill to create an indentation in the first surface to receive the keel of the implant; the drill may include a first drilling portion having a first diameter and a second drilling portion having a second diameter larger than the first diameter; the planar tool, rotary tool, and drill may each be adapted to removably connect to an end of a robotic arm; the method may further include removing at least one of the planar tool or the rotary tool from the end of the robotic arm and connecting the drill to the end of the robotic arm; the method may further include placing an implant adjacent to the first and second surfaces of the bone; the implant may include a distal planar surface at least partially formed of a porous material, and the step of placing the implant may be carried out without use of an adhesive; the distal planar surface of the implant may be in substantially continuous contact with the first surface of the bone; the bone may be a femur, and the method may further include securing a press-fit component to the femur; and the planar tool may be a saw, the rotary tool may be a burr, and the saw and the burr may be adapted to interchangeably connect to the end of a robotic arm.

In another embodiment, a method for bone preparation may include superimposing a first virtual boundary on a virtual bone; and superimposing a second virtual boundary on the virtual bone, wherein a planar surface of the second virtual boundary may be offset from and substantially parallel to a planar surface of the first virtual boundary.

The method may additionally or alternatively include one or more of the following features or steps: the virtual bone may represent a tibia; the planar surface of the first virtual boundary may be configured to guide a robotic arm to cut a bone with a first tool to create a first surface; the planar surface of the second virtual boundary may be configured to guide the robotic arm to extend the first surface of the bone with a second tool; and the second virtual boundary may be offset in a superior direction with respect to the first virtual boundary.

In yet another embodiment, a computer system for controlling a medical robotic system for preparing a bone of a patient may include an electronic storage device storing instructions for controlling the medical robotic system; and a processor configured to execute the instructions to: determine a first virtual boundary for a first tool based on received patient parameters; determine a second virtual boundary for a second tool based on the received patient parameters, wherein the first tool is different than the second tool; and constrain motion of the medical robotic system based on the first virtual boundary and the second virtual boundary.

The computer system may additionally or alternatively include one or more of the following features: the processor may be further configured to execute instructions to position and align, in six degrees of freedom, at least one of the first or second tools; constraining motion of the medical robotic system may include constraining motion of the first tool and constraining motion of the second tool; and the processor may be further configured to execute instructions to: determine a third virtual boundary for a third tool based on the received patient parameters, wherein the third tool is different than the first and second tools, and constrain motion of the third tool based on the third virtual boundary.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description serve to explain the principles of the disclosure.

FIG. 9 illustrates a guidance module monitor showing an image of a second virtual volume, according to an exemplary embodiment.

FIG. 10 illustrates working boundaries corresponding to the second virtual volume shown in FIG. 10, according to an exemplary embodiment.

DETAILED DESCRIPTION

Overview

The present disclosure is drawn to methods and systems for planning and performing bone repair procedures. The methods disclosed in this application may be performed using a robotic surgical device and may allow a practitioner to plan for or perform bone repair procedures using multiple tools. During the disclosed procedures, use of different tools may allow the prepared bone surfaces to match the shape of the bone-contacting surfaces of implant components.

When referring to specific directions with respect to a human body, the term "proximal" means closer to the heart and the term "distal" means more distant from the heart. The term "inferior" means toward the feet and the term "superior" means toward the head. The term "anterior" means toward the front of the body or the face and the term "posterior" means toward the back of the body. The term "medial" means toward the midline of the body and the term "lateral" means away from the midline of the body. When directions are used with respect to a user of a device, "proximal" means closer to the user and "distal" means farther away from the user.

EXEMPLARY EMBODIMENTS

Surgical System Overview

Figure 1:
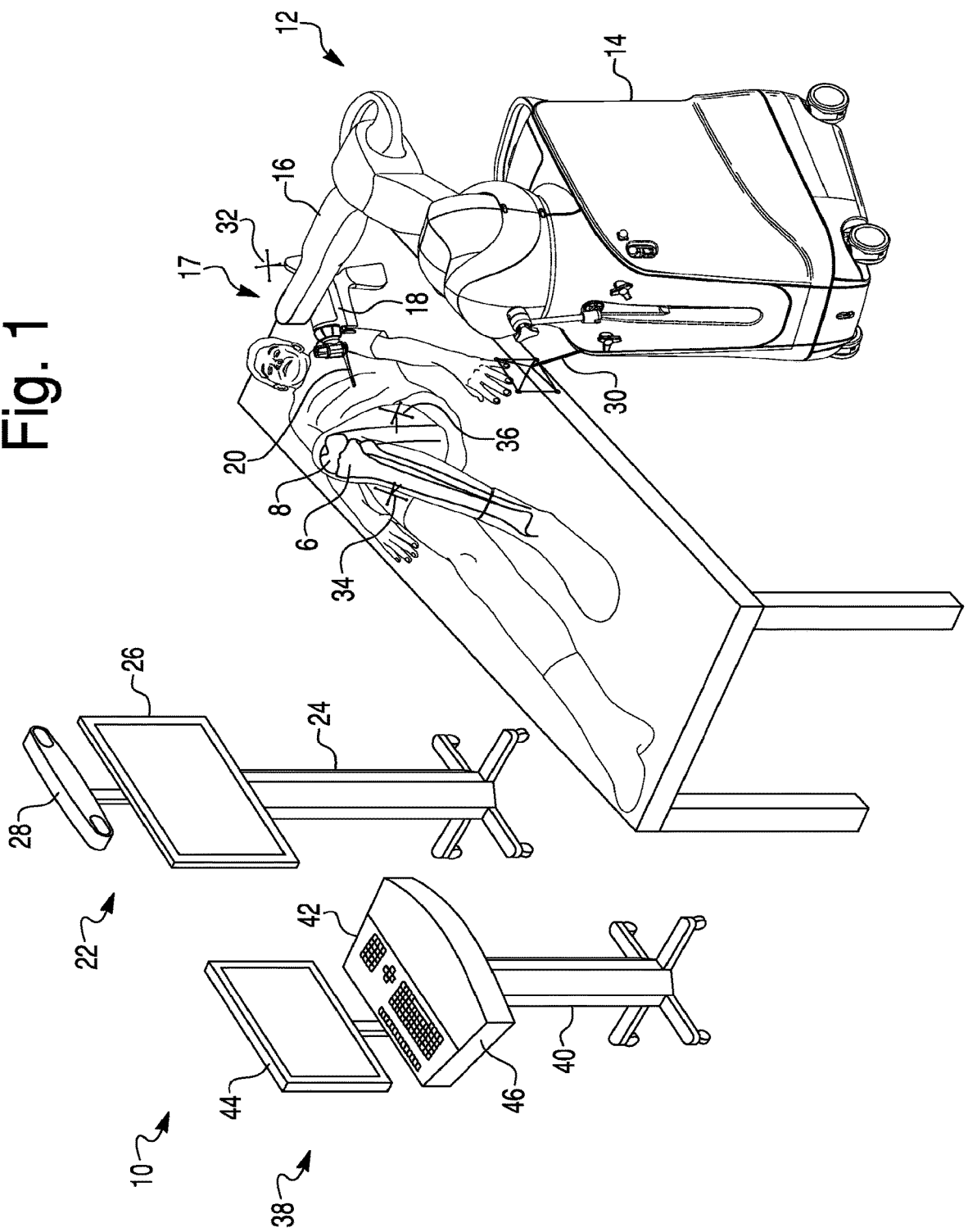
FIG. 1 illustrates a surgical system, according to an exemplary embodiment.

Referring to FIG. 1, according to an exemplary embodiment, a surgical system 10 may include a robotic device 12, a navigation system 22, and a guidance module 38. In general, a medical practitioner, such as a surgeon, may use the robotic device 12 to perform bone repair procedures as described in this application. The navigation system 22 may track the patient's bone, as well as the robotic device 12, to allow the surgeon to visualize the bone and tools on one or more displays 26, 44 during a procedure. The guidance module 38 provides an interface for a user to, for example, receive output from the surgical system in the form of instructions and other guidance, and to provide input to the system, such as modifications or adjustments to a bone repair plan. The guidance module 38 may house a computer 46, including the hardware and software required for execution of the processes described in this disclosure. The robotic device 12, the navigation system 22, and the guidance module 38 may all be in communication with each other via wired or wireless connections in order to guide the robotic device 12 during a procedure.

Figure 2:
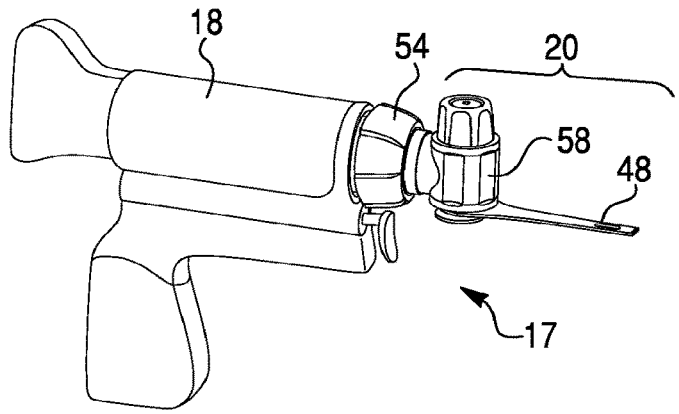
FIG. 2 illustrates a planar tool attachment, according to an exemplary embodiment.

The robotic device 12 may include a base 14, an arm 16, and a tool system 17. The base 14 may support the arm 16 and may be positionable near the patient. The arm 16 may include several links, and may be movable by the user to position and orient the tool system 17. The tool system 17 may include a tool body 18 and a tool attachment 20. The tool body 18 may be located at a distal end of the arm 16. In one embodiment, the tool body 18, via the arm 16, may be positioned and oriented in six degrees of freedom. In an alternative embodiment, the tool body 18 may be positioned and oriented in more than six degrees of freedom. The tool body 18 may couple to the tool attachment 20, which is the portion of the tool system 17 that modifies bone. As shown in FIGS. 1 and 2, the tool attachment 20 may be a planar cutting tool such as a saw 48. However, as will be described in greater detail below, multiple types of tool attachments 20 may be interchangeably coupled to the tool body 18.

The navigation system 22 may include a stand 24, a monitor 26, a detection device 28, and one or more trackable elements 30, 32, 34, 36. The stand 24 may support the monitor 26 and detection device 28 and may be positionable in the operating room. The monitor 26 may display images that allow medical practitioners to view a surgical plan or the progress of a procedure. The detection device 28 may include one or more detectors that are used to detect the location of the trackable elements 30, 32, 34, 36, which are fixed securely to tracked objects. For example, trackable element 30 may be fixed to the base 14 of the robotic device 12, trackable element 32 may be fixed to the tool system 17, trackable element 34 may be fixed to a first bone of a patient (e.g., a tibia 6), and trackable element 36 may be fixed to a second bone of a patient (e.g., a femur 8).

The navigation system 22 may be any type of navigation system configured to track the pose (i.e., position and orientation) of a bone. For example, the navigation system 22 may be a non-mechanical tracking system, a mechanical tracking system, or any combination of non-mechanical and mechanical systems.

In one embodiment, referring to FIG. 1, the navigation system 22 may be a non-mechanical tracking system such as an optical tracking system. In one example of an optical tracking system, the detection device 28 may detect visible light and may be, for example, a MicronTracker (Claron Technology Inc., Toronto, Canada). In an additional or alternative example, the detection device 28 may include a stereo camera pair sensitive to infrared radiation.

The trackable elements 30, 32, 34, 36 may be configured to be "visible" by the type of detection device 28 being used. Depending on the detection device 28, the trackable elements may be active (e.g., light-emitting diodes or LEDs) or passive (e.g., reflective spheres, a checkerboard pattern, etc.) and have a unique geometry (e.g., a unique geometric arrangement of the markers) or, in the case of active markers, a unique firing pattern.

In operation, the detection device 28 detects positions of the trackable elements 30, 32, 34, 36, and the surgical system 10 (e.g., the computer system 46, which may include embedded electronics associated with the detection device 28) calculates a pose of the tracked objects, to which the trackable elements are fixed, based on the trackable elements' positions, unique geometry, and known geometric relationship to the tracked object.

The guidance module 38 may include a stand 40, an input device 42, a monitor 44, and a computer system 46. The stand 40 may support the input device 42, monitor 44, and computer system 46. The input device 42 may be a keyboard, mouse, or any other interface that allows the user to provide information to the surgical system 10. In an additional or alternative embodiment, the monitor 44 may include a touch screen that serves as the input device. Similar to monitor 26, the monitor 44 may display images that allow medical practitioners to view a surgical plan or the progress of a surgical procedure.

The computer system 46 may include a processor and an electronic storage device. The components of the computer 46 may be housed anywhere within surgical system 10. Additionally or alternatively, all or portions of the computer 46 may be housed in a remote location. The processor can be implemented as a general purpose processor, an application specific integrated circuit (ASIC), one or more field programmable gate arrays (FPGAs), a group of processing components, or other suitable electronic processing components. The electronic storage device (e.g., memory, memory unit, etc.) may be one or more devices (e.g., RAM, ROM, Flash memory, hard disk storage, etc.) for storing data and/or computer code for completing or facilitating the various processes and functions described in the present application. The electronic storage device may be or include volatile memory or non-volatile memory. The electronic storage device may include database components, object code components, script components, or any other type of information structure for supporting the various activities described in the present application. In one embodiment, the electronic storage device is communicably connected to the processor via the computer 46 and includes computer code for executing (e.g., by the processor) one or more processes described herein.

Tool System

Figure 3:
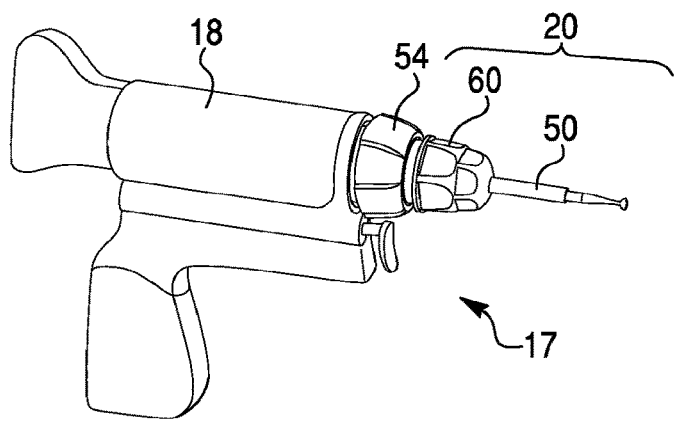
FIG. 3 illustrates a burr attachment, according to an exemplary embodiment.
Figure 4:
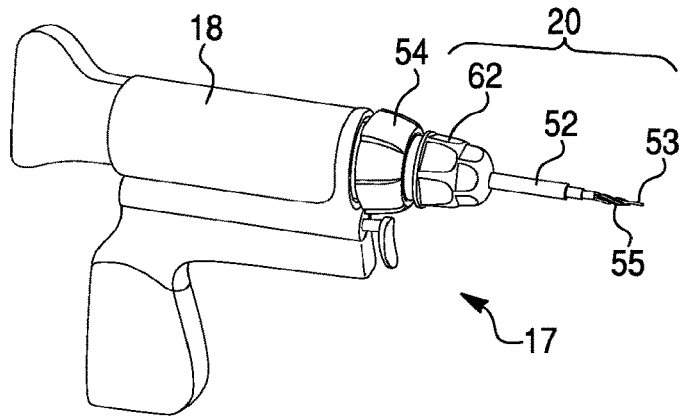
FIG. 4 illustrates a drill attachment, according to an exemplary embodiment.

As noted above, the tool system 17 may include a tool body 18 and a tool attachment 20. The tool body 18 may be interchangeably coupled to a variety of tool attachments 20 that may be used during the procedures described herein. Each of the tool attachments 20 may be connected to, removed from, or reconnected to the end of the tool body 18, and thus the end of the robotic arm 16, during a surgical procedure. Referring to FIGS. 2-4, for example, the tool attachment 20 may be a planar tool, such as a saw 48, or a rotary tool, such as a burr 50 or a drill 52.

Referring to FIG. 2, in one embodiment, the saw 48 may be an oscillating saw with a cutting surface on its distal end. During operation, the saw 48 may oscillate around an axis, such as an axis perpendicular to the plane of the blade 48 (e.g., in FIG. 2, the saw 48 may oscillate in and out of the page). In other embodiments, the saw 48 may oscillate around an axis that is oriented differently with respect to the tool body 18 or portions of the saw 48. Although saw 48 is shown as straight, saw 48 may alternatively be bent, changing the angle of the cutting surface. The oscillating saw may be a sagittal saw. In another embodiment, the planar tool may be a reciprocating saw (e.g., a blade or a rasp). Reciprocating saws may have a cutting surface along a longitudinal edge (e.g., a blade) or may have a planar surface with teeth (e.g., a rasp). In some embodiments, the planar tool may be a wire saw.

Referring to FIG. 3, the burr 50 may have a portion at its distal end that rotates around a longitudinal axis and may be operated to remove tissue or bone. The distal tip of the burr 50 may be curved, flattened, oval, irregularly-shaped, or any other shape. Referring to FIG. 4, the drill 52 may also rotate around a longitudinal axis and may be operated to remove tissue or bone. In one embodiment, the drill 52 includes a first drilling portion 53 having a first diameter and a second drilling portion 55 having a second diameter larger than the first diameter. A drill having more than one diameter may be beneficial when preparing bone to receive different portions of implant components.

The tool attachment 20 may be any other type of rotary tool, such as a router. In yet another embodiment, the tool attachment 20 may be a waterjet used to remove tissue or for irrigation. The tool attachment 20, however, may be any type of tool used to modify or remove tissue or bone. Modifications may include cutting, carving, sculpting, filing, grinding, drilling, deforming, or any other way of modifying tissue or bone consistent with the type of tool attachment 20 and the motion of the tool attachment 20.

The tool body 18 may include a connection member 54, which may be configured to receive different adaptors 58, 60, 62. The adaptors 58, 60, 62 allow their corresponding attachments 48, 50, 52 to be coupled to and controlled by the tool body 18. For example, when connected to the tool body 18, the adaptor 58 may include a mechanism to allow the saw 20 to oscillate around a vertical axis through the adaptor 58. In contrast, the adaptors 60, 62 for rotary cutting tools may allow the burr 50 and drill 52, respectively, to rotate around a longitudinal axis through the adaptors 60, 62.

Implant System

Figure 5:
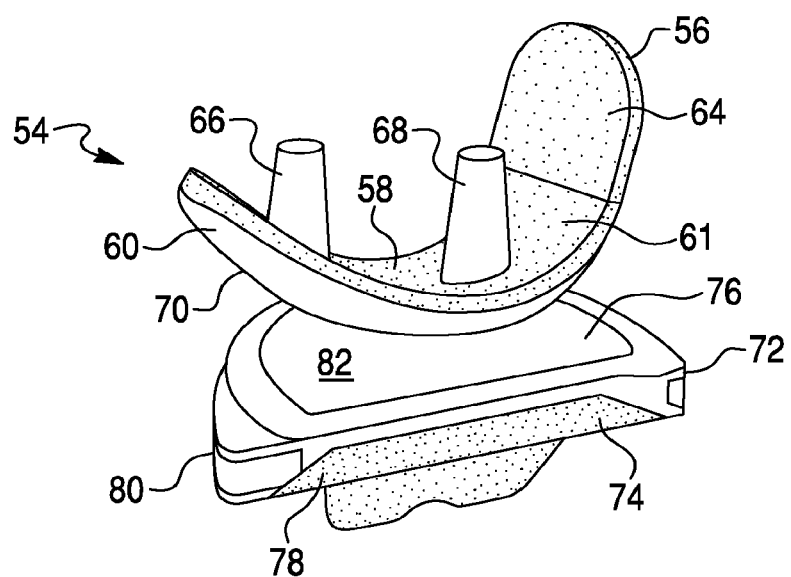
FIG. 5 illustrates femoral and tibial components of an implant system, according to an exemplary embodiment.
Figure 6:
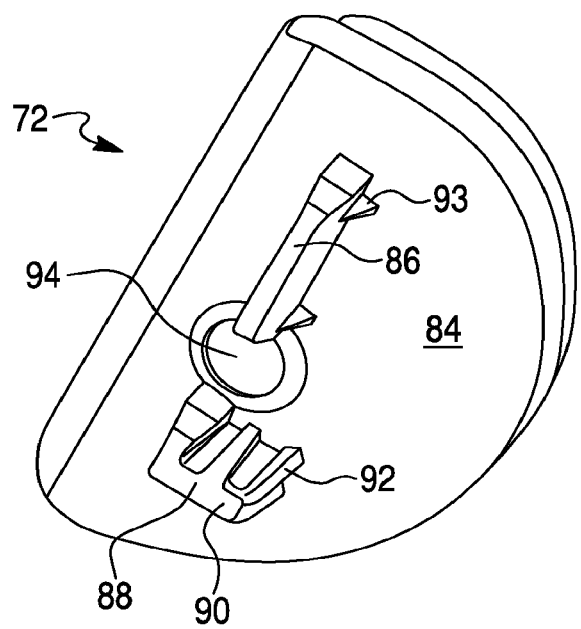
FIG. 6 illustrates an inferior perspective view of the tibial component, according to an exemplary embodiment.

FIG. 5 illustrates an implant system 54 that may be implanted using the procedures described in this application. The implant system 54 may include a femoral component 56 and a tibial component 72, referred to generally as "implant components." FIG. 6 illustrates an inferior perspective view of the tibial component 72. The femoral component 56 may be implanted on a distal end of a femur and may be designed to replace the articular surface of a femoral condyle, and the tibial component 72 may be implanted on a proximal end of a tibia and may be designed to replace the articular surface of a tibial condyle.

The femoral component 56 may include a femoral base 58 and a femoral articular portion 60. When implanted, the femoral base 58 may be fixed to the femur, and the femoral articular portion 60 may be fixed to the femoral base 58. The bone-contacting surface of the femoral base 58 may include a substantially planar surface 64 and a curved surface 61. In the embodiment shown in FIG. 5, the substantially planar surface 64 may contact a posterior surface of the femur. The femoral articular portion 60 may include a curved articular surface 70, which may contact the corresponding articular surface 76 of the tibial component 72.

The femoral component 56 may further include a first post 66 and a second post 68 protruding proximally from the femoral base 58. In one embodiment, the first post 66 is an anterior post, and the second post 68 is a posterior post. The posts 66, 68 may be frustrums, cylindrical, or any other elongated shape protruding from the articular surface of the femoral component 56. In one embodiment, the posts 66, 68 may include elongated ridges (not shown) extending in the proximal-distal direction along the outer surface of posts 66, 68.

The tibial component 72 may include a tibial base 74 and a tibial articular portion 76. When implanted, the tibial base 74 may be fixed to the tibia and the tibial articular portion 76 may be fixed to the tibial base 74. The tibial component 72 may be generally D-shaped and include a first side wall 78 and a second side wall 80. The first side wall 78 may be substantially planar, and the second side wall 80 may be curved. The tibial articular portion 76 may include an articular surface 82. In one embodiment, the articular surface 82 may be concave. In an alternative embodiment, the articular surface 82 may be planar.

As shown in FIG. 6, the bone-contacting surface of the tibial base 74 may include an inferior surface 84 and one or more elongated keels 86, 88 protruding from the surface 84. The inferior surface 84 may be planar. The keel 86 may extend in an anterior-posterior direction, and the keel 88 may extend in a medial-lateral direction. In one embodiment, the keels 86, 88 are generally perpendicular to each other.

The keels 86, 88 may have one or more extensions 92. The extensions 92 may extend laterally from the main body portions of keels 86, 88. For example, in FIG. 6, extension 92 may extend in an anterior-posterior direction from the main body 90 of keel 88. The extensions 92 may be wedge-shaped and may taper to become more narrow as they extend distally from the inferior surface 84. The extensions 92 may be the same height as the keels 86, 88.

The keels 86, 88 may additionally or alternatively have one or more fins 93. The fins 93, like the extensions 92, may protrude from the main body of the keels 86, 88. The fins 93 also may be wedge-shaped, and they may taper to a narrow point as they extend distally from the inferior surface 84. In one embodiment, the fins 93 are about half of the height of the keels 86, 88. The tibial base 74 may further include an aperture 94 through which another device, instrument, or material (e.g., a bone screw) can be inserted to, for example, help secure the tibial base 74 to the tibia 6.

The femoral component 56 and the tibial component 72 may be constructed from any combination of solid metal, porous metal, polymers, or other materials. The femoral base 58 and the tibial base 74 may be made of a metal such as titanium or stainless steel. In one embodiment, the femoral and tibial bases 58, 74 are made of a porous metal designed to facilitate bone ingrowth, as described in U.S. patent application Ser. No. 14/212,051, filed Mar. 14, 2014, titled "Unicondylar Tibial Knee Implant," and incorporated by reference herein in its entirety. The femoral and tibial articular portions 60, 76 may be made of a polymer material such as PEEK. In some embodiments, portions of the implant components, such as the femoral or tibial bases 58, 74, may include more than one type of material. For example, portions of femoral and tibial bases 58, 74 may be made of a porous material while other portions are made of non-porous material.

In some embodiments, the implant system 54 may include only the tibial component 72 or only the femoral component 56, or may include both the femoral component 56, the tibial component 72, and a patella-femoral component for implantation on the anterior surface of the femur. Although a medial left tibial component 72 and femoral component 56 are illustrated in the drawings, the implant system 54 may include any subset and combination of the following implant components: 1) medial left tibial component; 2) medial left femoral component; 3) lateral left tibial component; 4) lateral left femoral component; 5) medial right tibial component; 6) medial right femoral component; 7) lateral right tibial component; 8) lateral right femoral component; and 8) patella-femoral component on the anterior surface of the femur. The various implant components may be designed to accommodate the different anatomy of the left and right leg bones and the medial and lateral articular surfaces of each bone.

In other embodiments, the implant system 54 may include implant components for other bones or joints. For example, the implant components may be for implantation on a patient's acetabulum or any other bone, including bones in the ankle, shoulder, or spine. The implant components may be for use in a joint or outside of a joint. For example, the implant components may be a plate and screws to repair a bone fracture. The methods described herein may be used to prepare bone to receive implants of different shapes and having different bone-contacting surfaces.

The preparation of the bone to accept implant components of the implant system 54 may be facilitated by the various devices and methods described in this application. In general, once the bone is prepared, an implant component may be secured to the bone. In one embodiment, one or more implant components are secured to bone using methyl methacrylate, generally termed bone cement. In other embodiments, implant components may be secured to the bone directly, i.e., without bone cement. Fixation of an implant component to the bone without bone cement may be called cementless fixation or press-fit fixation.

Guidance Using Virtual Boundaries

The surgical system 10, including the navigation system 22, the computer system 46, and the robotic device 12, may be used to guide a medical practitioner during a surgical procedure. Guided bone modifications may be implemented using the above-described tool system and may prepare bone for receiving the above-described implant components.

Prior to the surgical procedure, the patient's anatomy (e.g., tibia and femur) may be scanned using any known imaging technique, such as CT or MRI. The scan data may then be segmented to obtain a three-dimensional representation of the patient's anatomy. The images of the patient's anatomy may be used during pre-operational planning to determine approximate placement of the implant components.

Once the patient is in the operating room, the navigation system 22 may be used to determine the pose (i.e., position and orientation) of the patient's anatomy relative to the detection device 28. To determine the pose of the tibia and femur, for example, trackable elements 34, 36 are attached to those bones. Any known registration process may then be used to register the physical anatomy (e.g., the tibia and femur) to the virtual representation of the anatomy created beforehand (e.g. the preoperative three-dimensional representation). Registration is the process of correlating two coordinate systems, for example, by using a coordinate transformation process. One registration process may include the point-based registration technique described in U.S. Pat. No. 8,010,180, filed Feb. 21, 2006, titled "Haptic Guidance System and Method," and incorporated by reference herein in its entirety. Once registered, the patient's anatomy can be tracked by the navigation system 22 during the procedure, and the computer system 46 may continuously update the virtual representations on one or both of the monitors 26, 44 in correspondence with movement of the patient. Registration of the patient's anatomy therefore allows for accurate navigation during the surgical procedure and enables, as described further below, the virtual boundaries to correspond to working boundaries in physical space.

The surgical system 10 may guide a user during a surgical procedure by using a surgical plan having virtual boundaries. Virtual boundaries exist in virtual space, but they may represent (i.e., correspond to) planned constraints or boundaries on movement of the tool attachment 20 in physical space (i.e., they may represent "working boundaries" in physical space). For example, in various embodiments, virtual boundaries may represent desired tool pathways, desired limits or boundaries on tool movement, desired bone modifications (e.g., cuts), or desired volumes of bone to be removed. Virtual boundaries may be lines, planes, curved surfaces, volumes, or boundaries of a volume. Virtual boundaries can take any shape or form to facilitate guidance of the tool attachment 20. Although the term virtual volume is used in the examples below, the term virtual boundary refers to a virtual volume itself or to a portion of a virtual volume (e.g., a boundary of a volume).

Figure 7:
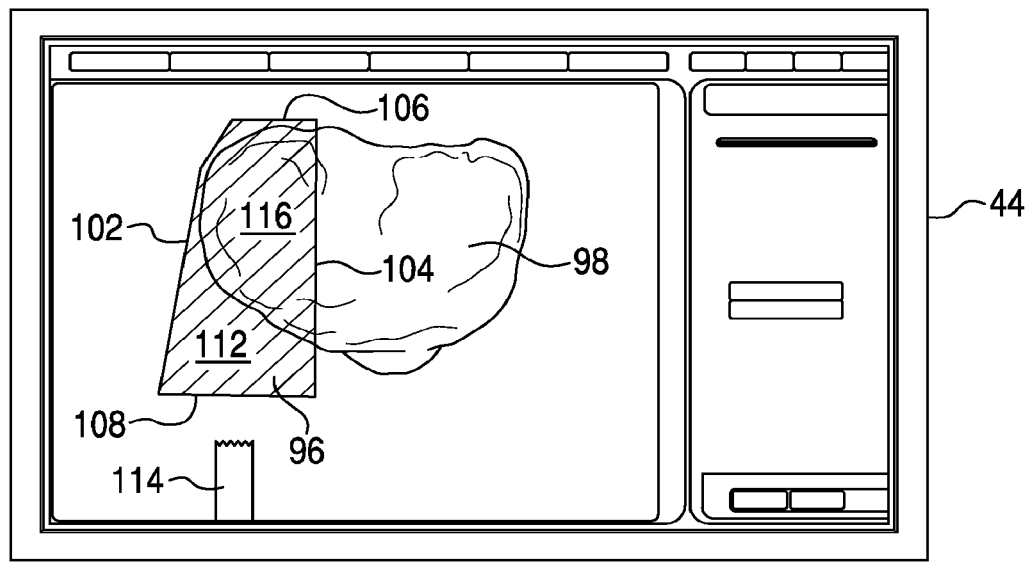
FIG. 7 illustrates a guidance module monitor showing an image of a first virtual volume, according to an exemplary embodiment.
Figure 12:
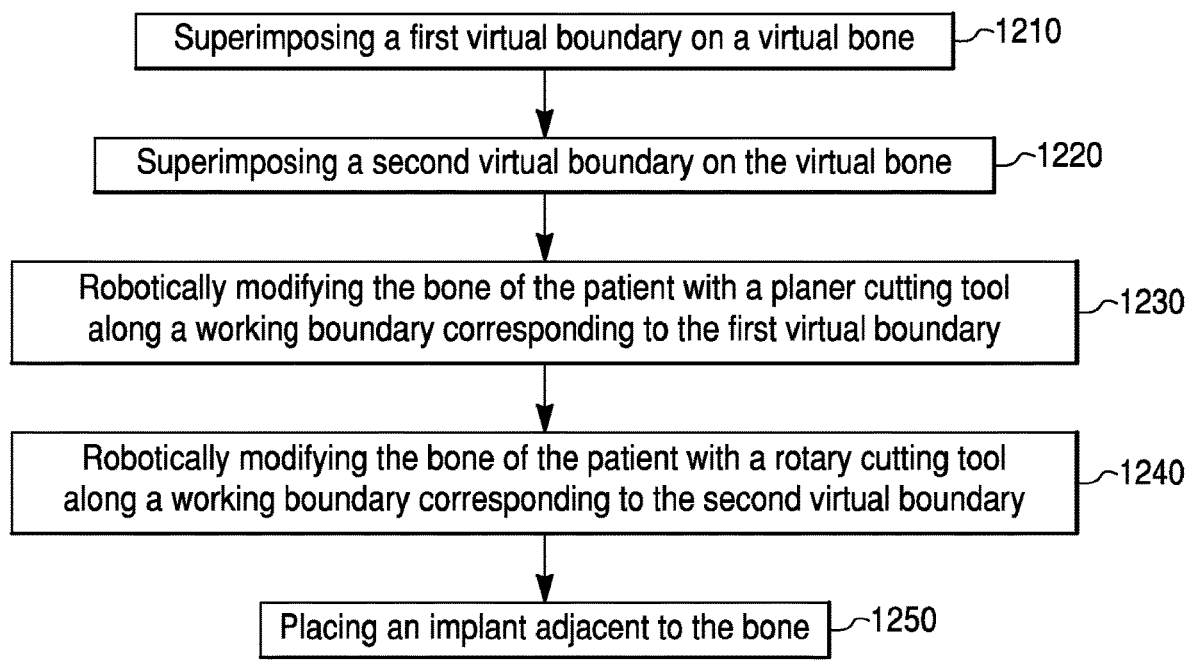
FIG. 12 is a method flow chart illustrating an exemplary method for repairing a bone.

FIG. 7 illustrates a superior view of a first virtual volume 96 superimposed on a virtual bone 98. FIG. 7 also shows a virtual tool attachment 114, which represents physical tool attachment 20 (in FIGS. 7 and 8, tool attachment 20 may be a planar tool 48). The image may be displayed intraoperatively on monitor 44 or monitor 26. In this example, first virtual volume 96 may have a trapezoidal top surface, although the surfaces of the virtual volume 96 may be any shape and size. The virtual bone 98 may represent a tibia, although in other surgical plans the virtual bone 98 may represent a femur, an acetabulum, a bone of the ankle, shoulder, spine, or arm, or any other bone. For reference, FIG. 12 depicts an anterior view of first virtual volume 96 and a second virtual volume 100.

First virtual volume 96 may represent (i.e., correspond to) boundaries constraining tool attachment 20 (in this example, planar tool 48 represented by virtual tool 114). For example, several boundaries or outer surfaces of first virtual volume 96 may represent constraints on tool attachment 20. First virtual volume 96 may include an anterior boundary 108, a medial boundary 102, a posterior boundary 106, a lateral boundary 104, an inferior boundary 110 (see FIG. 12), and a superior boundary 112. Each of the boundaries may be "active" or "inactive" at different times during a surgical procedure. An active boundary may represent a constraint in physical space (e.g., a surface that constrains tool attachment 20), while an inactive boundary may allow tool attachment 20 to cross. In the embodiment shown in FIG. 7, anterior surface 108 may be inactive, meaning the corresponding working boundary in physical space would not constrain the tool attachment 20. In contrast, boundaries 102, 106, 104, 110, and 112 may be active, meaning their corresponding working boundaries in physical space may constrain tool attachment 20 and prevent substantial movement past the boundaries.

In an additional or alternative embodiment, first virtual volume 96 may represent (i.e., correspond to) a volume of bone to be removed. In one example, the portion of virtual volume 96 that intersects the virtual bone 98, depicted as region 116 in FIG. 7, represents a volume of bone to be removed during the surgical procedure. In one embodiment, the outer boundaries of the region 116, the volume of bone to be removed, may be represented by portions of inferior boundary 110, lateral boundary 104, and the edges of the virtual bone 98 medial to the lateral boundary 104.

Figure 8:
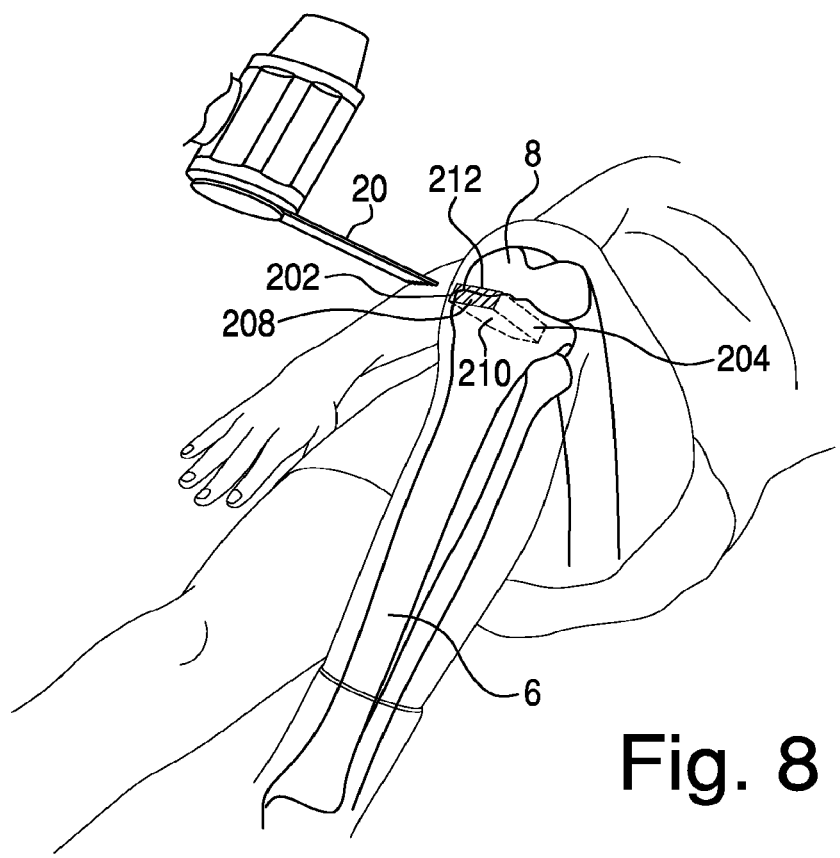
FIG. 8 illustrates working boundaries corresponding to the first virtual volume shown in FIG. 7, according to an exemplary embodiment.

FIG. 8 illustrates the working boundaries that correspond to the virtual boundaries shown in FIG. 7. Working boundaries are the locations in physical space that correspond to the virtual boundaries of the surgical plan. Thus, based on the virtual boundaries of the surgical plan, the surgical system 10 may constrain movement of the tool attachment 20 along or past working boundaries. In this example, working boundaries 208, 202, 206 (not shown), 204, 210, and 212 may correspond, respectively, to virtual boundaries 108, 102, 106, 104, 110, and 112. During a procedure, the surgical system 10 may constrain movement of the tool attachment 20 when a user attempts to move the tool attachment 20 past any of the active working boundaries. In one embodiment, working boundaries 202, 206, 204, 210, and 212 may be active during a portion of the procedure. Thus, although tool attachment 20 may be permitted to pass inactive working boundary 208 to cut bone, the tool attachment 20 would not be permitted to pass the other working boundaries. In this manner, the surgical system 10 helps control removal of bone and other tissue according to the surgical plan.

FIGS. 9 and 10 illustrate another embodiment of a set of virtual boundaries (FIG. 9) and corresponding working boundaries (FIG. 10) that may be used to constrain movement of tool attachment 20 during a surgical procedure. Referring to FIG. 9, a second virtual volume 100 may be superimposed on a virtual bone 98. The second virtual volume 100 may be employed to constrain tool movement before, during, or simultaneously with the first virtual volume 96. Second virtual volume 100 may have many of the same characteristics as first virtual volume 96. However, in one embodiment, second virtual volume 100 may have a different shape and different placement relative to virtual bone 98. For example, second virtual volume 100 may have an irregularly-shaped top surface, as can be seen in FIG. 9, although the second virtual volume 100 may have surfaces of any shape and size.

Similar to first virtual volume 96, second virtual volume 100 may represent (i.e., correspond to) boundaries in physical space that may impose constraints on movement of tool attachment 20 (burr 50 in FIGS. 9 and 10). Second virtual volume 100 may include an anterior boundary 128, a medial boundary 122, a posterior boundary 126, a lateral boundary 124, an inferior boundary 130 (FIG. 12), and a superior boundary 132. At different times during the procedure, each of these boundaries may be active or inactive. In one embodiment, anterior boundary 128 is inactive to allow tool attachment 20 to cross the corresponding working boundary.

Again similar to first virtual volume 96, second virtual volume 100 may represent (i.e., correspond to) a volume of bone to be removed. As shown in FIG. 9, a region 136 of virtual volume 100 may overlap with virtual bone 98. The region 136 representing bone to be removed may be defined by all or portions of inferior boundary 130 (see FIG. 12), lateral boundary 124, medial boundary 122, the superior surface of virtual bone 98, the anterior surface of virtual bone 98, and the posterior surface of virtual bone 98. Each of the virtual boundaries of second virtual volume 100 may correspond to working boundaries, described further below. Similarly, the exterior surfaces of virtual bone 98 correspond to exterior surfaces of a physical bone, such as tibia 6. Accordingly, the boundaries of the volume of bone to be removed are represented by virtual boundaries/virtual bone in virtual space and working boundaries/bone in physical space.

FIG. 10 illustrates the working boundaries that correspond to the virtual boundaries of second virtual volume 100 shown in FIG. 9. Working boundaries 228, 222, 226 (not shown), 224, 230, and 232 correspond to virtual boundaries 128, 122, 126, 124, 130 and 132, respectively. Similar to the embodiment of FIGS. 7 and 8, the working boundaries may define boundaries across which the tool attachment 20 (burr 50 in FIGS. 9 and 10) is constrained from crossing. The working boundaries may be active or passive in any combination during a surgical procedure. In one embodiment, one portion of a procedure, all working boundaries except anterior working boundary 228 are active. Working boundary 228 may remain inactive during the procedure to permit the tool attachment 20 to cross working boundary 228 and modify bone.

Figure 11:
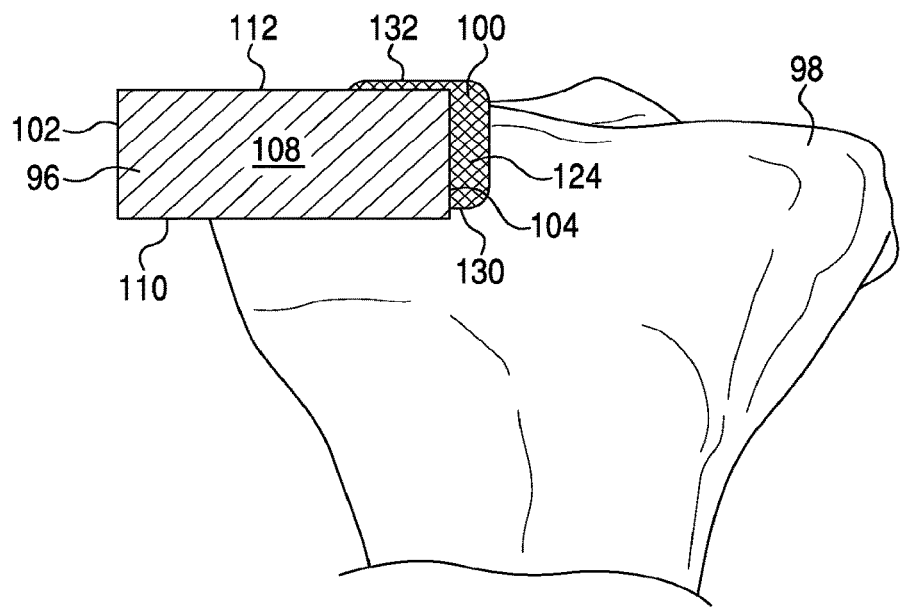
FIG. 11 illustrates the first and second virtual volumes superimposed on a virtual bone, according to an exemplary embodiment.

FIG. 11 illustrates an anterior view of the first virtual volume 96 and the second virtual volume 100 superimposed onto a virtual tibia 98. In one embodiment, the first virtual volume 96 and the second virtual volume 100 may be used/activated at different times during a surgical procedure to guide a tool attachment 20. Thus, the virtual volumes 96, 100 may each create corresponding working boundaries during different portions of the procedure.

The two virtual volumes 96, 100 are shown together in FIG. 11 to illustrate their relationship to each other. The second virtual volume 100 may be offset in the medial-lateral direction from the first virtual volume 96. In the embodiment of FIG. 11, the second virtual volume 100 may be offset in the lateral direction, although the direction might change depending on the surgical procedure to be completed, or for knee repair procedures, which knee and which condyle is being prepared to receive an implant. For example, the lateral virtual boundary 124 of the second virtual volume 100 may be located in a more lateral position than the lateral virtual boundary 104 of the first virtual volume 96. The second virtual volume 100 also may be offset from the first virtual volume 96 in the superior-inferior direction. In the embodiment of FIG. 11, the second virtual volume 100 may be offset in the superior direction. For example, inferior virtual boundary 130 of second virtual volume 100 may be offset in the superior direction from the inferior virtual boundary 110 of the first virtual volume 96. In addition or alternatively, the superior virtual boundary 132 of the second virtual volume 100 may be offset in the superior direction from the superior virtual boundary 112 of the first virtual volume 96. The offset surfaces of the first and second virtual volumes 96, 100 may be substantially parallel to each other or may have a different angle relative to each other. The first and second virtual volumes 96, 100 may be offset to optimize the final configuration of the bone that is prepared during the surgical procedure. These benefits will be explained further below in the "Bone Preparation Method" section.

In general, to constrain movement of the tool attachment 20, the surgical system 10 may map the virtual boundaries of the surgical plan, such as the virtual boundaries of first virtual volume 96 and second virtual volume 100, onto the patient's bone to create working boundaries. As described earlier, the navigation system 22 may track the location of the tool attachment 20 and one or more bones 6, 8. The tool attachment 20 is represented virtually (i.e., the tool attachment 20 properties and dimensions are stored in the surgical system 10), and as described earlier, the patient's bones are registered with the three-dimensional images used in the surgical plan. The tracking and registration information allows the surgical system 10 to map the virtual boundaries of the surgical plan onto the physical bone, such as tibia 6, to create working boundaries. When the patient moves, the virtual boundaries and therefore the working boundaries are updated. When the tool attachment 20 contacts or passes a working boundary, the surgical system 10 (via the computer system 46) may cause forces to be applied to the robotic arm 16. These forces may act to constrain further movement of the tool attachment 20.

Bone Preparation Method

Referring to FIG. 12, in an exemplary method, the surgical system 10, including the tool system 17, is used to implement a surgical plan. The surgical plan may include first and second virtual volumes 96, 100 and may guide preparation of one or more of a patient's bone to receive implant components, such as the components of implant system 54.

In one embodiment, multiple tool attachments 20 are used during the surgical procedure. Each tool attachment 20 can be removed from and reconnected to the distal end of the robotic arm 16 by removing/reconnecting the tool attachments 20 to the tool body 18. In one example, during a first portion of the procedure, a planar tool (e.g., saw 48) may be used to modify bone. During a second portion of the procedure, a rotary tool (e.g., burr 50 or drill 52) may be used to modify bone. In an additional or alternative embodiment, the burr 50 may be used during a second portion of the procedure and the drill 52 may be used during a third portion of the procedure. In yet another additional or alternative embodiment, an oscillating saw may be used during a first portion of a procedure, and a reciprocating saw may be used during a second portion of a procedure. It should be understood that "first portion," "second portion," and "third portion" do not necessarily designate order, but rather serve to distinguish between different portions of the procedure. One or more of a planar tool, such as an oscillating or reciprocating saw, a burr 50, or a drill 52 (e.g., one, two, three, four, or more tools) may be used during a procedure, and any tools that are used during the procedure may be used in any order. Accordingly, each tool attachment 20 may be connected, removed, or reconnected to the tool body 18 and the distal end of the robotic arm 16 during a surgical procedure.

A bone may be modified to include first and second surfaces. The first and second surfaces may correspond to bone-contacting surfaces of any type of implant. For example, the first surface may receive to a bone-contacting surface of a tibial component, femoral component, or plate, and the second surface may receive another bone-contacting surface of the tibial component, femoral component, or plate. The first and second surfaces may be planar, curved, cylindrical, or any other shape corresponding to a surface of the implant (e.g., corresponding to a main bone-contacting surface, a peg, a keel, a screw hole, etc.).

In one embodiment, during a first portion of a surgical procedure, the first virtual volume 96 may be used or activated to constrain movement of a planar tool (e.g., saw 48 or any other planar tool). The first virtual volume 96 may therefore be superimposed onto a virtual bone 98 (Step 1210). During this first portion of the procedure, the planar tool may be used to create a first surface. The first surface may be a planar surface on the patient's tibia 6. This planar surface may be, for example, along working boundary 210 shown in FIG. 8 (Step 1230). As the practitioner cuts into the tibia 6, the tool attachment 20 may be constrained from cutting inferior to working boundary 210. The end of tool attachment 20 also may be constrained from cutting posterior to working boundary 106. The remaining working boundaries of first virtual volume 96 may similarly constrain movement of the planar tool attachment 20.

In this manner, the first virtual volume 96 may guide the user to create a first surface that is an exposed planar surface along the patient's tibia. The planar surface may be located near a proximal end of the patient's tibia 6 and may be oriented substantially perpendicular to a longitudinal axis through the tibia 6. This planar surface, created along working boundary 210, may be referred to as the "tibial floor." The tibial floor created by the planar tool may be configured to receive a tibial component 72 implanted on (e.g., adjacent to) the tibial floor. An implant component may be adjacent to a bone when it is touching the bone or near the bone. In one embodiment, when implanted, the inferior surface 84 of the tibial component 72 may be in substantially continuous contact with the tibial floor. In other embodiments, either during tibia repair procedures or procedures on other bones, the first surface may have a non-planar shape and may, for example, includes curves or ridges.

During a second portion of the surgical procedure, the second virtual volume 100 may be used or activated to constrain movement of a rotary cutting tool (e.g., burr 50 or drill 52). During this portion, the second virtual volume 100 may be superimposed onto virtual bone 98 (Step 1220). The rotary tool may be used to create a second surface of the tibia 6. The second surface may be along lateral working boundary 224, which corresponds to lateral virtual boundary 124 (Step 1240). Lateral working boundary 224, along with the other working boundaries of second virtual volume 100, may constrain the rotary tool within the bounds of the second virtual volume 100.

The second virtual volume 100 may therefore guide the user to create a second surface that is an exposed surface substantially perpendicular to the exposed planar surface created by the planar cutting tool. The exposed surface created by the rotary cutting tool may be located near a proximal end of the patient's tibia 6 but may be oriented substantially parallel to a longitudinal axis through tibia 6. The surface created by the rotary cutting tool along working boundary 224 may be referred to as the "tibial wall." In other embodiments, either during tibia repair procedures or procedures on other bones, the second surface may have any other angle relative to the first surface. In another embodiment, the second surface may be created with planar tool 48.

In other embodiments, when the prepared bone is a femur or other bone, the first and second virtual volumes may constrain or guide movement of a tool along surfaces of the femur or other bone. Similar to repairs of the tibia, during bone repair procedures of the femur or any other bone, the first and second virtual volumes may correspond to working boundaries and may facilitate robotic modifications to create first and second surfaces that are desired and suitable for the specific bone repair procedure. The first and second surfaces may be perpendicular to each other or may have another angle relative to each other. The methods described herein may be implemented on an area of a bone that forms a joint (e.g., on an articular surface) or on a portion of a bone outside of a joint (e.g., the shaft of a long bone).

The positioning of the first virtual volume 96 with respect to the second virtual volume 100 may help ensure that, after implantation, the inferior surface 84 of tibial implant component 72 is in continuous contact with the tibial floor. The tibial floor may be considered the surface along working boundary 220 created by the planar tool, as described above, plus any "extension" of the tibial floor created by the rotary tool. The extension of the tibial floor can be seen in FIG. 11 as the portion of virtual boundary 130 (of the second virtual volume 100) that protrudes in a lateral direction from the lateral boundary 104 (of the first virtual volume 96). Once both the planar tool and the rotary tool have been used to sculpt the tibial floor in this area, the prepared tibial floor of the patient may have a similar surface. In other words, the tibial floor of the prepared bone may have a planar surface along working boundary 220 (of the first virtual volume 96), a slight step, and then a shorter planar surface along working boundary 230 (of second virtual volume 100). This step in the bone may be flattened when implant component 72 is implanted onto the prepared surfaces of the tibia 6, ensuring a snug fit between the component 72 and the prepared tibial floor. In other embodiments, the structural differences between the planar tool and the rotary tool will cause the final tibial floor to be smooth, without a step, even when the inferior boundary 130 of the second virtual volume 100 is offset in a superior direction from the inferior boundary 110 of the first virtual volume 96.

The offset of the second virtual volume 100 relative to the first virtual volume 96 may minimize the stress riser at the junction between the first and second surfaces. For example, during a bone repair procedure of a tibia, if an indentation were created between the tibial floor and the tibial wall, there might be a larger stress riser at the junction of the bone surfaces than if no indentation were created. The offset between the first and second virtual volumes helps to ensure that the junction between the bone surfaces includes a step or is continuous, rather than including an indentation.

In an additional or alternative embodiment, a third portion of the surgical procedure may include using drill 52 to drill one or more indentations (e.g., channels, holes) in tibia 6 or femur 8. For example, one or more indentations in tibia 6 may be drilled to receive keels 86 or 88. Similarly, one or more indentations in femur 8 may be drilled to receive posts 66, 68. A third virtual volume may guide drill 52 during creation of indentations by, for example, constraining movement of drill 52 past working boundaries corresponding to the third virtual volume.

During the surgical procedure, various tools may be interchanged and alternately coupled to tool body 18. This allows a variety of types of bone modifications to be made during a single surgical procedure. In addition, use of various tools allows the bone to be accurately sculpted to receive implant components having different configurations of bone-contacting surfaces. The use of various tools also allows for the effective use of the different cutting characteristics of different tools to form the bone-contacting surfaces. In one embodiment, the bone may be prepared with multiple tools to receive a press-fit implant component. For example, creating a planar tibial floor with a planar tool, a tibial wall with a burr, and indentations with a drill may prepare the tibia 6 to receive a press-fit tibial implant component 72 such that bone ingrowth will securely fix the implant component 72 to the tibia 6.

Figure 13:
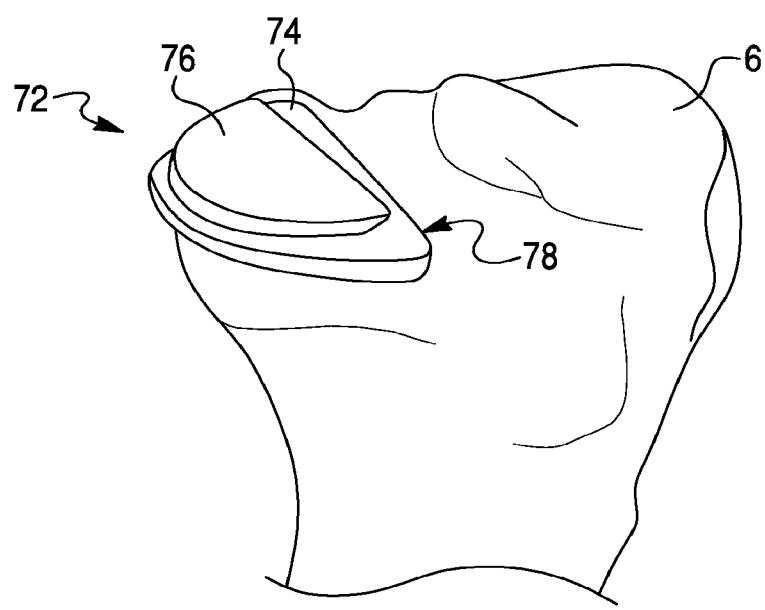
FIG. 13 illustrates a tibial component that has been implanted on the superior surface of a tibial condyle, according to an exemplary embodiment.

In one embodiment, surfaces of the tibia may be prepared to receive the first side wall 78 and second side wall 80 of tibial component 72. The bone surfaces may be prepared such that they will surround the outer surfaces of the tibial component 72 and hold the component in a press-fit manner. In some embodiments, to securely hold the implanted component, the prepared bone surfaces may surround an area that is slightly smaller than the tibial component 72. In another embodiment, the bone may be prepared with multiple tools to receive a cemented implant component or an implant component secured to the bone by any other fixation method. FIG. 13 illustrates tibial component 72 placed against the tibia 6 after the tibia 6 has been prepared as described herein (see Step 1250 of FIG. 12).

The surfaces of a femur may be prepared in accordance with the methods described herein to receive a femoral component 56 (see FIG. 5), which may be press-fit or cemented. For example, the bone surface corresponding to planar surface 64 may be a first surface prepared with a first virtual boundary and a planar tool, and other bone surfaces may be prepared with a second virtual boundary and a rotary tool and may correspond to and receive other bone-contacting surfaces of the femoral component 56. In one embodiment, the femoral surfaces may be prepared to directly match the bone-contacting surfaces of the femoral component. However, in another embodiment, the femoral surfaces may be prepared to partially deviate from the bone-contacting surfaces of the femoral component to ensure that the femoral component 56 is securely held by the bone.

To facilitate a secure press-fit, the bone surface corresponding to planar surface 64 and the bone surface corresponding to second post 68 may be prepared such that the bone between the planar surface 64 and second post 68 of the implanted component will be "squeezed," and the pressure will help hold the component 56 in place. Similarly, the surfaces corresponding to first post 66 and second post 68 may be prepared farther apart than the distance between the posts 66, 68 such that the bone between the implanted posts will be squeezed by the implanted posts. In yet another embodiment, the holes to receive posts 66, 68 may be prepared to be smaller than the posts themselves such that the posts are squeezed within their holes. The ability to use multiple tools during the surgical procedure, as well as the precise cuts allowed by the planar tool, may enhance a user's ability to prepare bone to receive a press-fit femoral component 56 or any other type implant component, whether or not the implant is secured to the bone by press-fit or by another method.

To facilitate a stable fit to the bone when an implant is secured to the bone with or without cement, the femoral surfaces may be prepared with enough deviation from the bone-contacting surfaces of the femoral component 56 such that errors in the execution of the bone modifications are biased to certain regions. For example, bone modifications may be executed to ensure that there is substantially continuous bone contact between planar surface 64 and the femur and between an anterior portion of curved surface 61 and the femur, leaving a region of diminished bone contact between the distal portion of the curved surface 61 and the femur. The amount of bone contact between two surfaces, such as the bone and a bone-facing implant surface, may be quantified by pressure between the two surfaces, by the percentage of the bone-facing implant surface that is touching the bone, or by any other method of measuring contact between two surfaces. The primary contact between the femoral component 56 and the bone in the anterior and posterior regions may ensure that the implant will rest stably on the bone, even if such primary contact causes diminished bone contact along portions of curved surface 61.

In one embodiment of a surgical procedure, a planar tool may be used to prepare bone surfaces to receive and/or contact the following features or surfaces of implant components: a) inferior surface 84 of tibial component 72, and b) the planar surface 64 of femoral component 56. A rotary tool may be used to prepare bone surfaces to receive and/or contact the following features or surfaces: a) side wall 78 of tibial component 72, b) curved surface 61 of femoral component 56; c) first post 66 and second post 68 of femoral component 56; and d) the bone-contacting surface and posts of a patello-femoral component, if being used.

In another embodiment, the planar tool may be used to prepare bone surfaces to receive and/or contact the following features or surfaces of implant components: a) inferior surface 84 of tibial component 72, and b) the planar surface 64 of femoral component 56. A first rotary tool, such as a burr, may be used to prepare bone surfaces to receive and/or contact the following features or surfaces: a) the side wall 78 of tibial component 72, b) the rim of aperture 94 of tibial component 72, and c) the curved surface 61 of femoral component 56. A second rotary tool, such as a drill, may be used to prepare bone surfaces to receive and/or contact the following features or surfaces: a) the first post 66 and second post 68 of femoral component 56; and b) the keels 86, 88 of tibial component 72.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A computer system for controlling a medical robotic system for preparing a bone of a patient, wherein the medical robotic system includes a power tool with planar and rotary attachments, the computer system comprising:
   an electronic storage device storing instructions for controlling the medical robotic system; and
   a processor configured to execute the instructions to:
      determine a first virtual boundary for the planar attachment based on received patient parameters;
      determine a second virtual boundary for the rotary attachment based on the received patient parameters;
      constrain motion of the planar attachment based on the first virtual boundary; and
      constrain motion of the rotary attachment based on the second virtual boundary.

2. The computer system of claim 1, wherein the processor is further configured to execute instructions to position and align, in six degrees of freedom, at least one of the planar attachment or the rotary attachment.

3. The computer system of claim 1, wherein constraining motion of the planar attachment includes constraining motion of the planar attachment along a first working boundary to create a first surface of the bone, wherein the first working boundary corresponds to the first virtual boundary.

4. The computer system of claim 1, wherein the processor is further configured to execute instructions to:
   determine a third virtual boundary for a third attachment based on the received patient parameters, wherein the third attachment is different than the rotary attachment and the planar attachment; and
   constrain motion of the third attachment based on the third virtual boundary.

5. The computer system of claim 1, wherein the bone is a tibia.

6. The computer system of claim 1, wherein the first virtual boundary is configured to guide a robotic arm to cut the bone with the planar attachment to create a first surface.

7. The computer system of claim 6, wherein the second virtual boundary is configured to guide a robotic arm to cut the bone with the rotary attachment to create a second surface.

8. A computer system for controlling a medical robotic system for preparing a bone of a patient, comprising:
   an electronic storage device storing instructions for controlling the medical robotic system; and
   a processor configured to execute the instructions to:
      determine a first virtual volume for a first tool based on received patient parameters, wherein the first virtual volume includes a first surface;
      determine a second virtual volume for a second tool based on the received patient parameters, wherein the first tool is different than the second tool, wherein the second virtual volume includes a second surface, and wherein the second surface is offset from the first surface; and
      constrain motion of the medical robotic system based on the first virtual volume and the second virtual volume;
      wherein the first tool and the second tool are attached to the same power tool mounted on an end of a robot arm.

9. The computer system of claim 8, wherein the first surface and the second surface correspond to bone contacting surfaces of an implant.

10. The computer system of claim 8, wherein the first surface is configured to receive a tibial component, a femoral component, or a plate of an implant; and wherein the second surface is configured to receive a tibial component, a femoral component, or a plate of an implant.

11. The computer system of claim 8, wherein the first surface and the second surface are planar surfaces.

12. The computer system of claim 8, wherein the first tool is a planar tool and the second tool is a rotary tool.

13. The computer system of claim 12, wherein the processor is further configured to execute instructions to:
   determine a third virtual volume for a third tool based on the received patient parameters, wherein the third tool is a drill; and
   constrain motion of the third tool based on the third virtual boundary.

14. The computer system of claim 12, wherein the planar tool is a saw, the rotary tool is a burr, and the saw and the burr are adapted to interchangeably connect to the end of the robotic arm.

15. The computer system of claim 8, wherein the first surface and the second surface are configured to receive a press-fit implant.

16. The computer system of claim 8, wherein the bone is a tibia, the first surface is a tibial floor, and the second surface is a tibial wall.

17. A computer system for controlling a medical robotic system for preparing a bone of a patient, comprising:
   an electronic storage device storing instructions for controlling the medical robotic system; and
   a processor configured to execute the instructions to:
      determine a first virtual volume for a first tool based on received patient parameters, wherein the first tool is an oscillating planar tool;
      determine a second virtual volume for a second tool based on the received patient parameters, wherein the second tool is a reciprocating planar tool; and
      constrain motion of the first tool based on the first virtual volume; and
      constrain motion of the second tool based on the second virtual volume;
      wherein the first tool and the second tool are attached to the same power tool mounted on an end of a robot arm.

18. The computer system of claim 17, wherein the processor is further configured to execute instructions to position and align, in six degrees of freedom, at least one of the first tool or the second tool.

19. The computer system of claim 17, wherein constraining motion of the first tool includes constraining motion of the first tool along a first working boundary to create a first surface of the bone, wherein the first working boundary corresponds to the first virtual boundary of the first virtual volume.

20. The computer system of claim 17, wherein the processor is further configured to execute instructions to:
   determine a third virtual volume for a third tool based on the received patient parameters, wherein the third tool is different than the first tool and the second tool; and
   constrain motion of the third tool based on the third virtual volume.

* * * * *